(12) United States Patent
Martinez et al.

(10) Patent No.: US 7,055,764 B1
(45) Date of Patent: Jun. 6, 2006

(54) TWO-PHASE EVAPORATOR DEVICE

(75) Inventors: José Antonio Muñoz Martinez, Barcelona (ES); Cedric Morhain, Barcelona (ES); Ruben Garcia Fabrega, Barcelona (ES); Andrea Caserta, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 0 days.

(21) Appl. No.: 11/022,527

(22) Filed: Dec. 21, 2004

(51) Int. Cl.
A01G 27/00 (2006.01)
A24F 25/00 (2006.01)
A61L 9/04 (2006.01)

(52) U.S. Cl. .................... 239/145; 239/44
(58) Field of Classification Search ........... 239/145, 239/44, 34, 45; 431/278, 298, 299, 126, 431/206; 422/120, 123, 125, 126; 222/187
See application file for complete search history.

(56) References Cited

U.S. PATENT DOCUMENTS

| 47,173 | A | * | 4/1865 | Speakman | 431/299 |
|---|---|---|---|---|---|
| 2,572,329 | A | * | 10/1951 | Foster | 239/45 |
| 3,633,881 | A | * | 1/1972 | Yurdin | 261/24 |
| 4,323,193 | A | * | 4/1982 | Compton et al. | 239/44 |
| 5,840,257 | A | * | 11/1998 | Bureau et al. | 422/125 |
| 6,899,280 | B1 | * | 5/2005 | Kotary et al. | 239/34 |

FOREIGN PATENT DOCUMENTS

| GB | 2 371 750 A | 8/2002 |
|---|---|---|
| WO | WO 2004/032620 A1 | 4/2004 |
| WO | WO 2004/032983 | 4/2004 |

* cited by examiner

Primary Examiner—David A. Scherbel
Assistant Examiner—Darren Gorman
(74) Attorney, Agent, or Firm—Fulwider Patton LLP

(57) ABSTRACT

It relates to an evaporator device of those which are used to diffuse fragrances, insecticides or other substances which are held in a recipient (1) in the form of two immiscible liquids. It comprises two wicks (2, 2') which extend from the interior of the recipient (1) in contact with the liquid or the liquids to the exterior where the evaporation area thereof is located, and a stopper cover (3) which closes the recipient (1) and which is traversed by the wicks (2, 2'). One of the wicks (2) has an impermeable layer (4) which extends from its lower extremity to the stopper cover (3) of the recipient (1) preventing contact with one of the liquids and enabling the ingress of the other liquid into the wick (2) only through its lower extremity, thereby allowing the independent egress of each liquid through each wick (2, 2').

4 Claims, 6 Drawing Sheets

TWO-PHASE EVAPORATOR DEVICE

FIELD OF THE INVENTION

The present invention relates to an evaporator device of those which are used to diffuse fragrances, insecticides or other substances which are held in a recipient in the form of two immiscible liquids.

An object of the invention is that the evaporator device incorporate means which establish independence between the wicks, so that each liquid is diffused specifically through only one of the wicks.

BACKGROUND OF THE INVENTION

Evaporator devices of active substances are known of the type which use liquids such as fragrances and insecticides for the diffusion thereof in the air, which come with a wick partially immersed in the liquid which enhances the dispersion of the liquid in the atmosphere on reaching the surface of the wick exposed to the air.

Commercial products are also known which contain two immiscible liquids, termed two-phase devices. This type of device combines the action of two liquids, for example a fragrance with a biocide, a fragrance with an odor neutralizer or a fragrance with an insecticide or any other combination of volatile substances with or without active ingredients.

The immiscible liquids generally differ in that one of them has an aqueous base while the other has an organic base, the two liquids remaining in two layers with a well defined interface, the liquid of less density being in the upper layer.

In the patent of invention GB 2 371 750 a device is disclosed which contains a recipient with a mixture of two phases of immiscible liquids of different appearance, one of them contains a fragrance component which on diffusing in the air determines that the mixture takes on a different appearance to the mixture and therefore indicative of the activation of the device.

Another type of device incorporates a wick and contains two liquids which rise by capillary action through the wick, the liquids being designed so that the proportions of the formula are maintained during the entire lifetime of the product, for which reason it is necessary to have a precise definition of the wick and of the liquids.

This is the case of the device described in the patent of invention WO 2004/032620, wherein the wick is a single wick which comprises a first section of porous material of a certain size and a second section of porous material of greater size than that of the first section, such that in an initial phase in which the need exists to obtain maximum diffusion, the propagation is established of the liquid through both sections and in a subsequent phase only the first section disperses vaporized liquid into the atmosphere which is consequently spread in a smaller amount than in the initial phase.

In the patent of invention WO 2004/032983 a diffusion system is described based on a wick for the diffusion of two liquids having different properties held in one container, the wick being defined by two halves of different materials, a first half for the diffusion of a first liquid and a second half for the diffusion of a second liquid.

The fact that the halves of the wick are specifically defined in accordance with the characteristics of the liquid implies a multiplication in the specifications of the wick, since any variation in the formula of the liquid signifies a change in the properties of said halves.

SUMMARY OF THE INVENTION

The two-phase evaporator device which constitutes the object of this invention proposes the employment of two wicks which can be or not of the same material and characteristics, which extend from the interior of a recipient in which are to be found two immiscible liquids to the exterior in an area in which the evaporation thereof takes place, be this spontaneous or enhanced by the effect of heat, by the flow of ventilation air or by other means, being distinguished fundamentally in that one of the two wicks has an impermeable layer which extends from its lower extremity to the stopper of the recipient preventing contact with the liquid held in an upper level and enabling the entrance into the wick of the liquid held at a lower level only through said lower extremity.

The other wick is in contact with the two liquids but it only carries the liquid located at the upper level to the evaporation area of the wick. The liquid held at a lower level which makes contact with this wick is impeded from rising because the way is blocked by the liquid located at the upper level which is saturating the wick.

The amount of liquid delivered from the evaporation area will depend on the characteristics of the material and on the section of the wicks, as well as the physicochemical characteristics of the actual liquids. Likewise the possibility to modulate or modify the evaporation of one of the liquids with respect to the other can be achieved by changing the volatility of both or by altering the section of one of the wicks with regard to the other, so that a greater evaporation surface provides more evaporated liquid.

In contrast to other solutions it is not necessary to have a different material for the wicks to assist in the separation of different types of liquid into each wick, instead the physical barrier which the impermeable layer establishes allows the independent egress of liquids and therefore it is possible to use the same material in the wicks. In any case it is envisaged that the two-phase evaporator device object of this invention can likewise make use of wicks of different material.

The possibility is optionally contemplated that, in the evaporation area above the stopper where the wicks are uncovered to facilitate evaporation, there be a separating layer between the wicks, which has a geometry similar to the interface between wicks and which avoids the spillage of liquid from one wick into the other.

In a possible embodiment it is considered that the overall section of the two-wick assembly and optionally of the separating layer have a geometry equivalent to that of a wick of a standard product, for which reason the container can be used with a standard heating device. In most products, this standard section would have a cylindrical geometry. In other possible embodiments the wicks can be of a prismatic configuration having a square, rectangular, triangular or other section.

The possibility is also envisaged that the protective layer of the wick and/or the impermeable layer form a single piece with the stopper of the recipient which will be obtained preferably by injection moulding.

Additionally the device can incorporate means to enhance the diffusion of the substances into the atmosphere through heating, ventilation or any other means.

BRIEF DESCRIPTION OF THE DRAWINGS

To complete the description which is being made and with the object of assisting in a better understanding of the characteristics of the invention, in accordance with a preferred practical embodiment thereof, accompanying this description as an integral part thereof, is a set of drawings wherein by way of illustration and nor restrictively, the following has been represented.

DETAILED DESCRIPTION OF THE INVENTION

Figure 1:
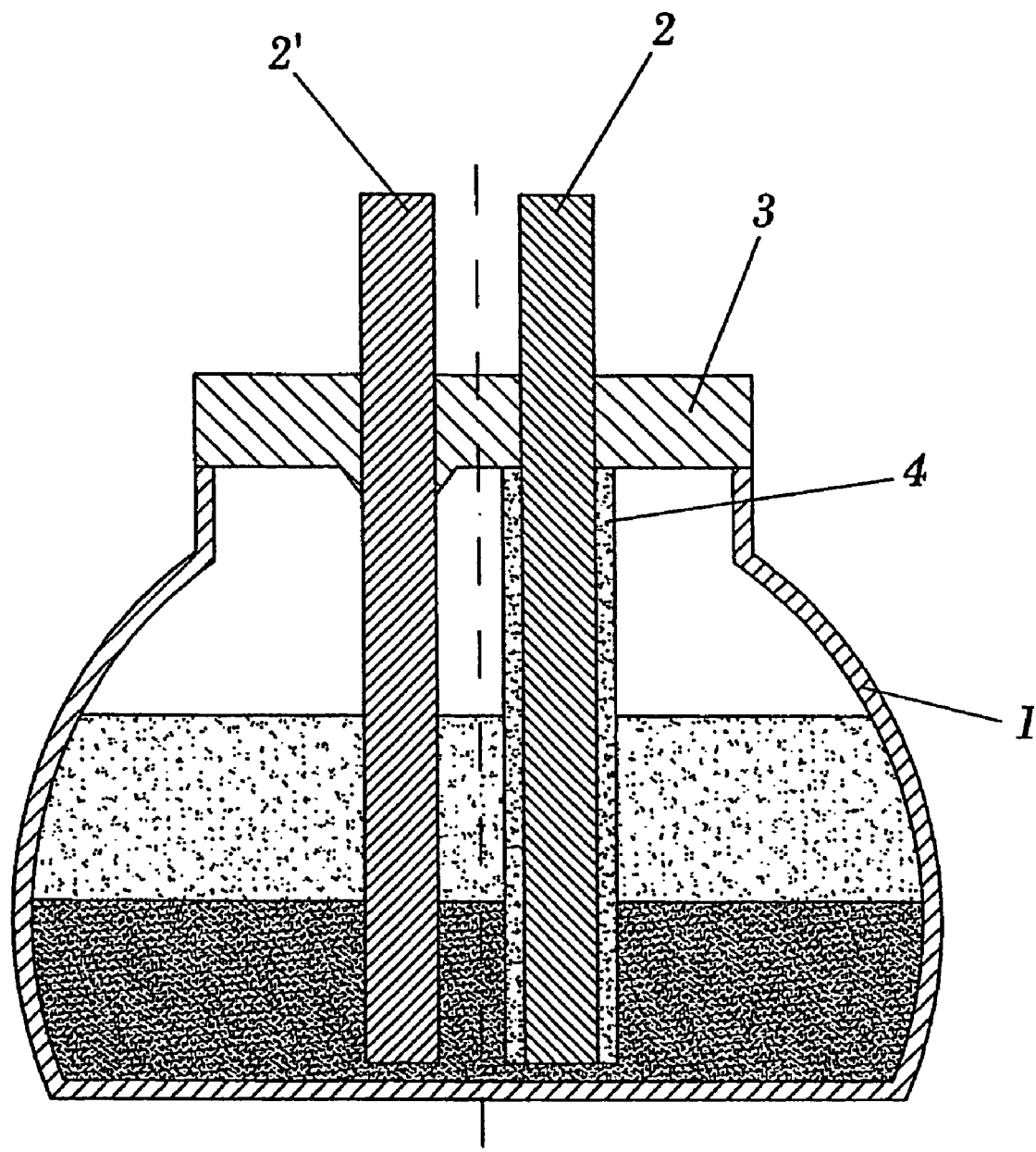
FIG. 1.—It shows a sectional view of a two-phase evaporator device which has an impermeable layer in one of its wicks in the inside of the recipient.

In the light of the figures a preferred embodiment of the two-phase evaporator device is described which constitutes the object of this invention.

As can be observed in said figures, this evaporator device is of the type of those which comprise a recipient (1) in which two immiscible liquids are held, two wicks (2, 2') which extend from the interior of the recipient (1) in contact with the liquid or the liquids to the exterior where their evaporation area is located, and a stopper cover (3) which closes the recipient (1) and which is traversed by the wicks (2, 2').

In general terms the evaporator device is fundamentally distinguished because one of the wicks (2) has an impermeable layer (4) which extends from its lower extremity to the stopper (3) of the recipient (1) preventing contact with one of the liquids and enabling the entrance of the other liquid into the wick (2) through its lower extremity only.

Figure 4:
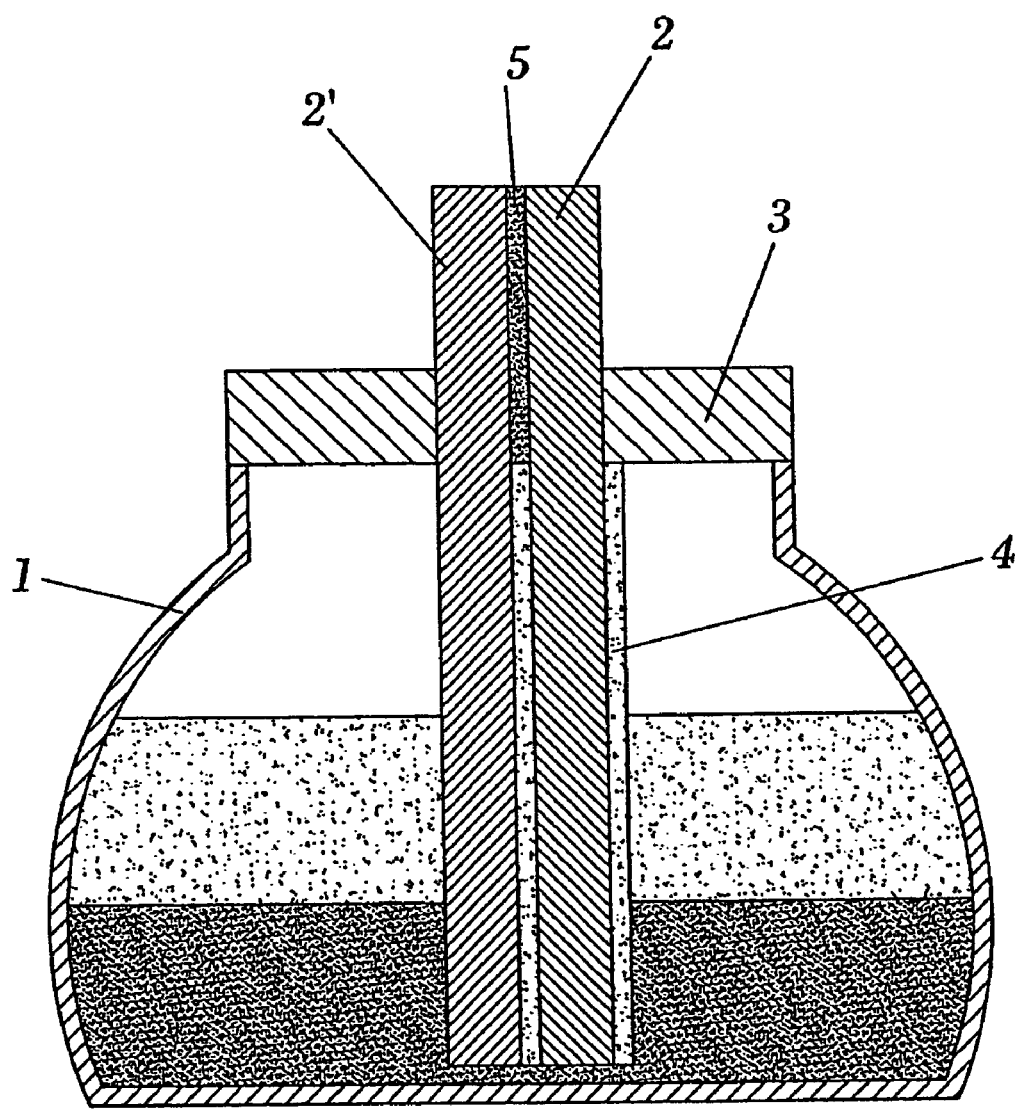
FIG. 4.—It shows a sectional view of the two-phase device which has an impermeable layer in one of the wicks and a separating layer in the area where the wicks are joined.
Figure 6:
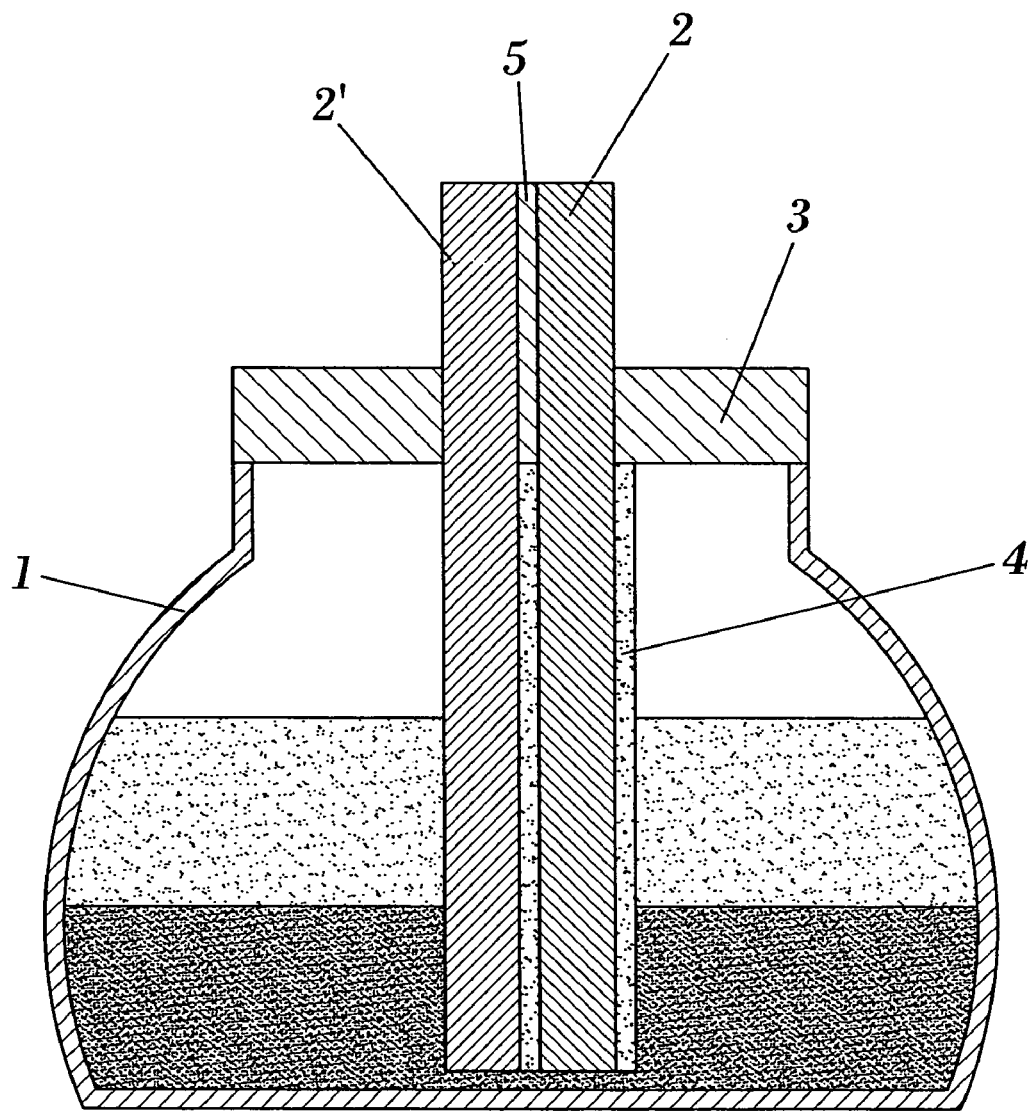
FIG. 6.—It shows a sectional view of the two-phase device which has an impermeable layer in one of the wicks and a separating layer in the area where the wicks are joined, the separating layer forming a single piece with the stopper cover of the recipient.

In a complimentary manner, as maybe observed in FIGS. 4 and 6, the wicks (2, 2') are separated by a separating layer (5) which prevents the liquid in one wick (2', 2) from coming into contact with the other wick (2, 2'), this separating layer (5) can form a single piece with the stopper cover (3) of the recipient (1), as shown in FIG. 6.

Figure 3:
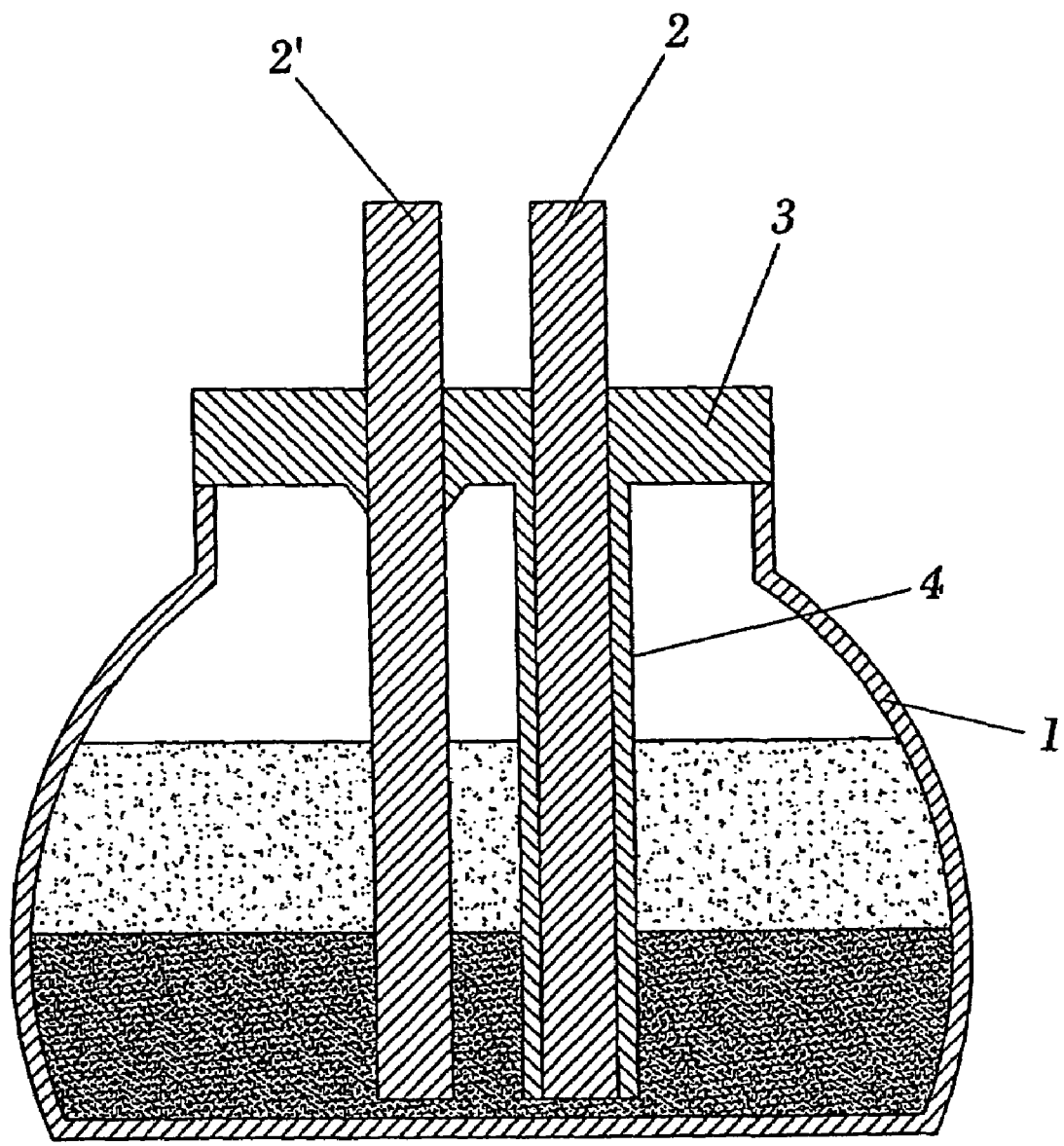
FIG. 3.—It shows a sectional view of the two-phase device which has the impermeable layer of one of the wicks forming part of the same piece as the stopper cover of the recipient.

In a possible constructional solution shown in FIG. 3 the possibility is envisaged whereby the impermeable layer (4) of the wick (2, 2') can form a single piece with the stopper (3) of the recipient (1), obtained preferably by injection moulding.

Figure 5:
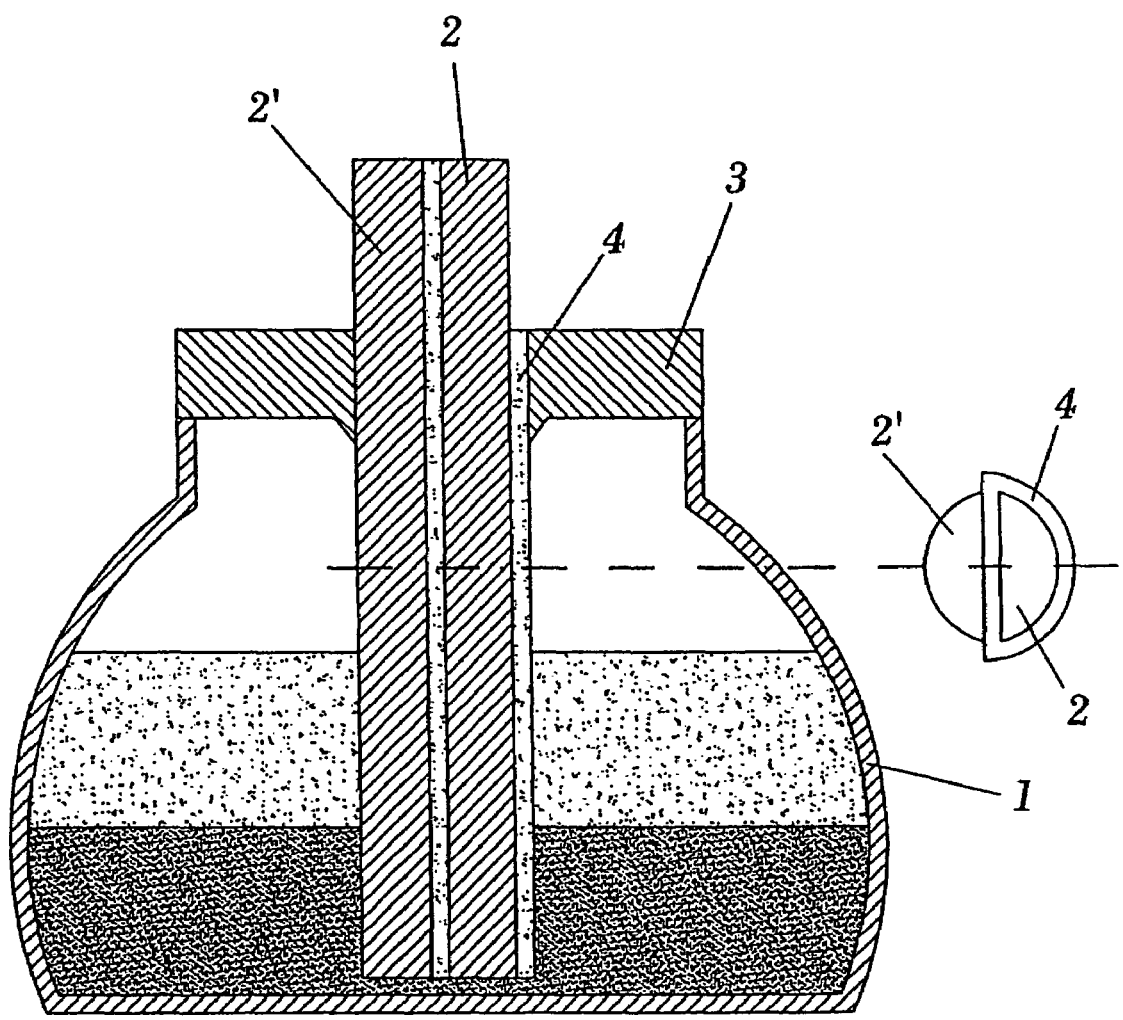
FIG. 5.—It shows a sectional view of the two-phase device which incorporates a compact assembly formed by the two wicks which traverse the cover, and also a cut is seen in which the section of the assembly can be observed.

Also in one of the possible embodiments, such as that envisaged in FIG. 5, one of the wicks (2') and the other wick (2) with its impermeable layer (4) can have a semicircular section over their full extension and the flat face of one of the wicks (2') is in contact with the flat face of the impermeable layer (4) of the other wick (2) forming a cylindrical assembly which traverses the stopper (3) of the recipient (1) in the assembled condition thereof.

Figure 2:
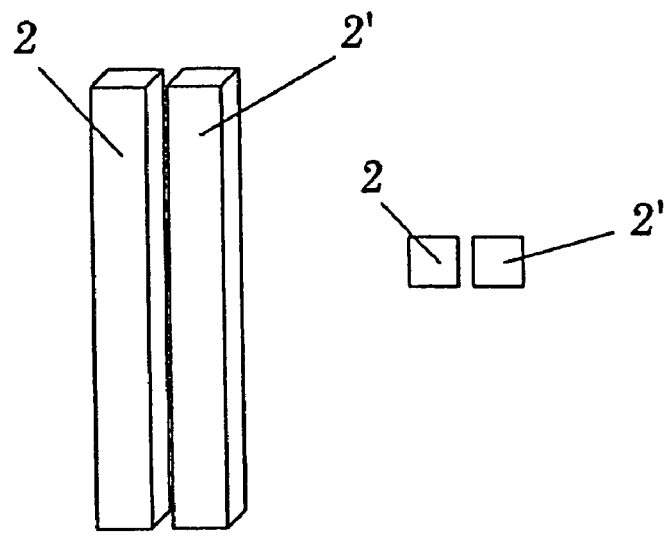
FIG. 2.—It shows a view in perspective of different possible configurations of the wicks.
Figure 2:
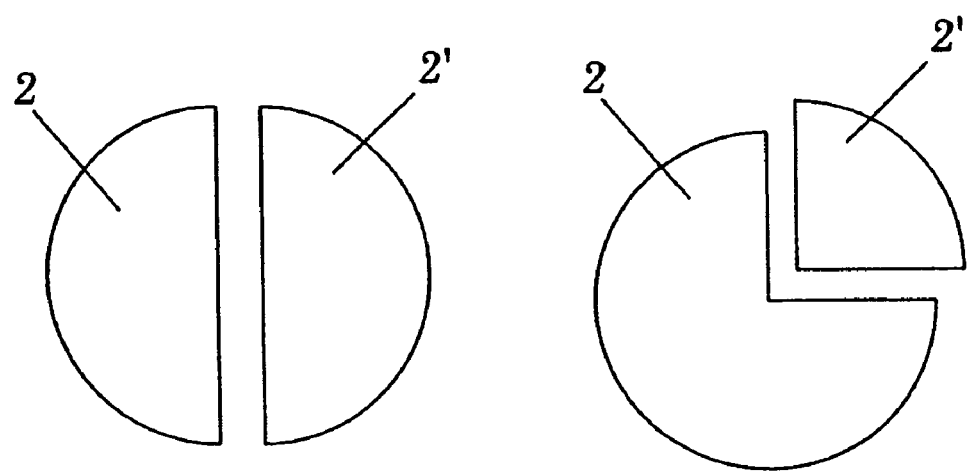
Figure 2:
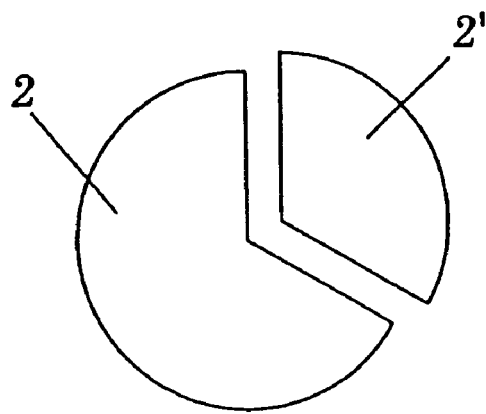

Other possible geometric forms are shown in FIG. 2, wherein wicks (2, 2') are to be seen with prismatic rectangular or partially circular forms with the same or different section.

We claim:

1. Two-phase evaporator comprising a recipient in which two immiscible liquids are held, a liquid located at an upper level and a liquid located at a lower level, two wicks which extend from the liquid located at said lower level and through the liquid located at said upper level to the exterior where the evaporation area thereof is located, and a stopper cover which closes the recipient and which is traversed by the wicks, wherein one of the wicks has an impermeable layer which extends from its lower extremity to the stopper cover of the recipient preventing contact with the liquid located at said upper level and enabling the entrance of the liquid located at said lower level into said wick through the lower extremity thereof only.

2. Two-phase evaporator device according to claim 1, wherein the wicks are separated in the evaporation area by a separating layer which prevents the liquid of one wick from entering in contact with the other wick.

3. Two-phase evaporator device according to claim 1, wherein the impermeable layer of the wick forms a single piece with the stopper cover of the recipient.

4. Two-phase evaporator according to claim 2, wherein the separating layer forms a single piece with the stopper cover of the recipient.

* * * * *